United States Patent
Chinn et al.

(10) Patent No.: US 8,664,433 B2
(45) Date of Patent: Mar. 4, 2014

(54) SYNTHESIS OF 4-[3-(2,6-DIMETHYLBENZYLOXY)PHENYL]-4-OXOBUTANOIC ACID

(75) Inventors: Jason P. Chinn, Cloverdale, CA (US); Robert J. Kaufman, St. Louis, MO (US); Shalini Sharma, Gaithersburg, MD (US); David Wirth, Oak Ridge, NC (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 365 days.

(21) Appl. No.: 12/990,851

(22) PCT Filed: May 4, 2009

(86) PCT No.: PCT/US2009/042660
§ 371 (c)(1),
(2), (4) Date: Jan. 11, 2011

(87) PCT Pub. No.: WO2009/137381
PCT Pub. Date: Nov. 12, 2009

(65) Prior Publication Data
US 2011/0201838 A1    Aug. 18, 2011

Related U.S. Application Data

(60) Provisional application No. 61/057,410, filed on May 30, 2008, provisional application No. 61/050,442, filed on May 5, 2008.

(51) Int. Cl.
*C07C 59/00* (2006.01)

(52) U.S. Cl.
USPC .......................................... 562/465

(58) Field of Classification Search
None
See application file for complete search history.

(56) References Cited

U.S. PATENT DOCUMENTS

| 4,716,178 | A | 12/1987 | Scherrer et al. |
| 7,101,910 | B2 | 9/2006 | Sharma et al. |
| 7,329,782 | B2 * | 2/2008 | Sharma .................. 568/309 |
| 7,361,686 | B2 | 4/2008 | Hodge et al. |
| 7,442,796 | B2 | 10/2008 | Sharma et al. |
| 7,514,555 | B2 | 4/2009 | Hodge et al. |
| 2004/0009984 | A1 | 1/2004 | Carpino et al. |
| 2006/0122222 | A1 | 6/2006 | Whitehouse et al. |

FOREIGN PATENT DOCUMENTS

WO    02100341 A2    12/2002

* cited by examiner

*Primary Examiner* — Karl J Puttlitz
(74) *Attorney, Agent, or Firm* — Lewis J. Kreisler

(57) ABSTRACT

The compound 4-[3-(2,6-Dimethylbenzyloxy)phenyl]-4-oxobutanoic acid (DPA) is synthesized from 1-[3-(2,6-Dimethylbenzyloxy)-phenyl]-ethanone (DPE) via the intermediate 4-[3-(2,6-Dimethylbenzyloxy)phenyl]-4-oxobulanoic acid ethyl ester (DPAE).

20 Claims, No Drawings

SYNTHESIS OF 4-[3-(2,6-DIMETHYLBENZYLOXY)PHENYL]-4-OXOBUTANOIC ACID

BACKGROUND OF THE INVENTION

A synthesis of 4-[3-(2,6-Dimethylbenzyloxy)phenyl]-4-oxobutanoic acid and its ethyl ester is described in WO 02/100341 A2 (Wellstat Therapeutics Corp.). There is a need for an improved synthesis that has good yield, purity, and, cost of goods.

DESCRIPTION OF THE INVENTION

This invention provides a method for producing a crude preparation of 4-[3-(2,6-Dimethylbenzyloxy)phenyl]-4-oxobutanoic acid ethyl ester, comprising the following steps: (a) to a first solution in a reaction vessel, adding dropwise a second solution while maintaining the solution in the reaction vessel under an inert gas at a temperature between −35° C. and −75° C. under stirring conditions, wherein the first solution consists essentially of one equivalent of 1-[3-(2,6-Dimethylbenzyloxy)-phenyl]-ethanone dissolved in tetrahydrofuran and 1,3-Dimethyl-3,4,5,6-tetrahydro-2(1H)-pyrimidinone, the first solution being cooled to a temperature between −35° C. and −75° C. and having a total water content of from 0.1 to 0.6 equivalents; and the second solution consists essentially of from 1.1 to 1.3 equivalents of lithium bis(trimethylsilyl)amide dissolved in tetrahydrofuran; (b) stirring the solution resulting from step (a) at a temperature between −35° C. and −75° C. for about 30 minutes; (c) to the solution from step (b), adding dropwise from 1 to 2 equivalents of ethyl bromoacetate while maintaining the temperature of the solution in the reaction vessel between −35° C. and −75° C.; (d) allowing the temperature of the solution from step (c) to warm to a temperature in a range from −40° C. to 0° C. and maintaining the solution at a temperature in said range for a sufficient time for completion of alkylation; (e) adding water or an aqueous salt solution to the solution from step (d) to quench; (f) to the organic solution from step (e), adding an organic solvent; (g) to the solution from step (f), separating the aqueous layer from the organic layer and discarding the aqueous layer; (h) washing the organic layer from the preceding step with a saturated aqueous sodium chloride solution; and (i) concentrating the organic layer from step (h) to an oil, thereby yielding crude 4-[3-(2,6-Dimethylbenzyloxy)phenyl]-4-oxobutanoic acid ethyl ester. A synthesis of the starting material, 1-[3-(2,6-Dimethylbenzyloxy)-phenyl]-ethanone (alternative name: 3-(2,6-Dimethylbenzyloxy) acetophenone) is described in WO 02/100341 on page 137. Alternatively 1-[3-(2,6-Dimethylbenzyloxy)-phenyl]-ethanone can be synthesized as described in Example 3.

In step (a) the first solution should not be saturated. Also, one would have expected that the inclusion of water would have given a worse result, but surprisingly it resulted in a decrease in impurities and a higher yield. In step (c) one should not use less than one equivalent of ethyl bromoacetate. Too much bromoacetate should also be avoided, as too much bromoacetate will yield a dialkylated product contaminant. In step (d), temperature is inversely correlated with the time needed for the alkylation reaction to complete. It is convenient to use a temperature of −25° C., in which case the alkylation reaction takes about ten minutes to complete.

In more specific embodiments of the above method, the temperature recited in one or more of steps (a), (b) and (c) is below −50° C. In an embodiment of the method, in step (a) the first solution has a total water content of 0.36 equivalents. In an embodiment of the method, in step (a) the number of equivalents of lithium bis(trimethylsilyl)amide in the second solution is from 1.15 to 1.2, for example 1.17. In an embodiment of the method, in step (c) the number of equivalents of ethyl bromoacetate is from 1.2 to 1.6, for example from 1.25 to 1.56. In an embodiment of the method the solution is maintained at a temperature of −25° C. for about ten minutes. In an embodiment of the method the aqueous salt solution is aqueous 10% ammonium chloride. In an embodiment of the method, in step (f) the organic solvent is selected from the group consisting of ethyl acetate, ethyl formate, propyl acetate, toluene, and methyl tert-butyl ether. In an embodiment of the method, between steps (h) and (i), the organic layer from step (h) is washed twice with water or a 4% aqueous solution, of either sodium chloride or ammonium chloride.

This invention provides a method for producing a crude preparation of 4-[3-(2,6-Dimethylbenzyloxy)phenyl]-4-oxobutanoic acid, comprising the following steps: (a) under stirring conditions in a reaction vessel, dissolving the 4-[3-(2,6-Dimethylbenzyloxy)phenyl]-4-oxobutanoic acid ethyl ester from the method described above in ethanol; (b) to the solution from step (a), adding 2 equivalents of sodium hydroxide solution compared to the amount of the ethyl ester and maintaining the solution in the reaction vessel at 55° C. for thirty minutes; (c) to the mixture from step (b), adding, water and removing the ethanol by evaporation; (d) to the solution from step (c), adding water: (e) washing the solution from step (d) with methyl t-butyl ether; (f) acidifying the solution from step (e) with concentrated hydrochloric acid and ethyl acetate to a pH of between 1 and about 3, preferably between 2 and 3; (g) to the solution from step (f), separating the aqueous layer from the organic layer and discarding the aqueous layer; (h) washing the organic layer from step (g) with water; (i) concentrating the organic layer from step (h) to a solid, thereby yielding crude 4-[3-(2,6-Dimethylbenzyloxy)phenyl]-4-oxobutanoic acid.

This invention provides a method for producing purified 4-[3-(2,6-Dimethylbenzyloxy)phenyl]-4-oxobutanoic acid, comprising: (a) in a reaction vessel, dissolving the crude solution containing 4-[3-(2,6-Dimethylbenzyloxy)phenyl]-4-oxobutanoic acid in ethanol and heating the resulting solution to 65° C.; (b) to the solution from the preceding step, adding water dropwise while maintaining the solution at a temperature of from 45° C. to 60° C. (in a more specific embodiment, from 50° C. to 60° C.), wherein the ratio of water added to the amount of ethanol from step (a) is about 4:6; (c) allowing the solution from step (b) to cool slowly under stifling conditions to produce a solid; and (d) isolating the solid from step (c), thereby yielding purified 4-[3-(2,6-Dimethylbenzyloxy)phenyl]-4-oxobutanoic acid. In a more specific embodiment of this method, between steps (a) and (b) the solution from step (a) is filtered through a medium glass frit. In more specific embodiments of this invention, in step (b) the temperature is from 50° C. to 60° C., more specifically from 50° C. to 55° C., still more specifically about 55° C. In an embodiment of this method, in step (c) the solution is allowed to cool slowly to room temperature. In a further embodiment of this method the following further steps are performed after step (d); (e) washing the solid from step (d) with 1:1 water/ethanol; (f) dissolving the solid from step (e) in ethanol to produce a solution; (g) to the solution from step (f), adding water dropwise while maintaining the solution at 55° C.; (h) allowing the solution from step (g) to cool slowly to room temperature under stirring conditions to produce a solid; (i) isolating the solid from step (h) and washing the solid with 1:1 water/ethanol and (j) drying the solid from step (i), thereby yielding further purified 4-[3-(2,6-Dimethylbenzyloxy)phenyl]-4-oxobutanoic acid.

As used herein the transitional term "comprising" is open-ended. A claim utilizing this term can contain elements in addition to those recited in such claim.

The invention will be better understood by reference to the following examples, which illustrate but do not limit the invention described herein.

EXAMPLES

Example 1

Lab Scale Synthesis

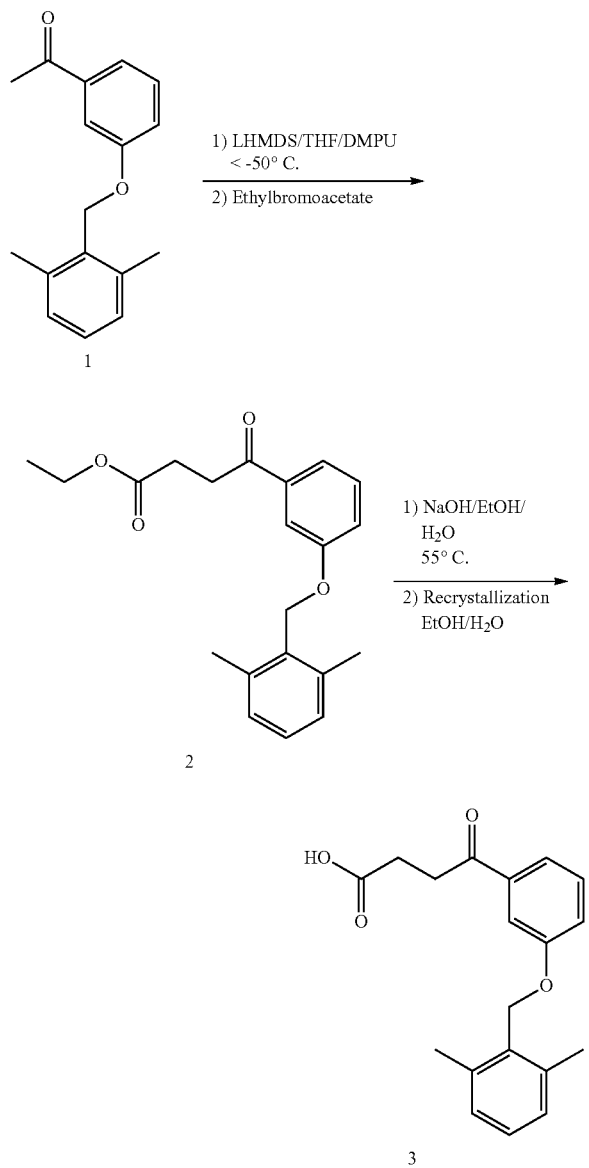

Compound 2:

To a 250 mL 3-neck flask with stir bar and thermocouple under argon was added 10 g of 1-[3-(2,6-dimethylbenzyloxy)-phenyl]-ethanone (DPE, 1) (39.32 mmol) which was dissolved into 41.9 mL of tetrahydrofuran (THF) and 15.9 mL of 1,3-dimethyl-3,4,5,6-tetrahydro-2(1H)-pyrimidinone (DMPU). The total moisture content was brought up to 14.16 mmol (0.36 equivalent to DPE, 1) by addition of 152 µL of water based on the water content of the THF and DMPU. The flask was cooled to below −50° C. in a dry ice/acetone bath and 38.7 mL of lithium bis(trimethylsilyl)amide solution (1.19 M in THF, 46.00 mmol) was added dropwise over 7 minutes keeping the temperature below −50° C. The solution was stirred an additional 30 minutes below −50° C. followed by the dropwise addition of 6.80 mL of ethyl bromoacetate (61.34 mmol) over two minutes to keep the temperature below −50° C. The bath was removed and the solution was allowed to warm to −25° C. and held at this temperature for 10 minutes, then allowed to warm to −20° C. and quenched by the addition of 41 mL of 10% ammonium chloride. The reaction mixture was taken in a separatory funnel, 20 mL of ethyl acetate was added, and the organic layer was then washed with 2×50 mL of 4% sodium chloride solution followed by 50 mL of saturated sodium chloride solution and concentrated to a dark oil. Analysis of the oil showed 74.78 area % of 4-[3-(2,6-dimethylbenzyloxy)-phenyl]-4-oxobutanoic acid ethyl ester (DPAE, 2).

Compound 3:

The dark crude DPAE oil, 2, was dissolved in 26 mL of ethanol in a 100 mL round bottom flask with a stirbar and 3.14 g of sodium hydroxide (78.64 mmol) dissolved in 12 mL of water was added and the reaction was placed into a 55° C. bath for 30 minutes. To the mixture 7.0 mL of water was added followed by concentration on a rotary evaporator until ethanol no longer condensed. This was followed by the addition of 24 mL of water, and using a separatory funnel the aqueous layer was washed with 4×24 mL, of methyl t-butyl ether. The solution was acidified stepwise by the addition of 2.5 mL of concentrated hydrochloric acid (conc. HCl), addition of 42 mL of EtOAc, and 5.3 mL of conc. HCl to lower the pH to approximately pH 1 by test strip analysis. The acidic aqueous layer was removed in a separatory funnel, and the organic layer was washed with 42 mL of water and concentrated to 103 g of a beige solid. HPLC analysis showed 92% 4-[3-(2,6-dimethylbenzyloxy)-phenyl]-4-oxobutanoic acid (DPA, 3) with 6.3% diacid as the major impurity.

Recrystallization: The crude DPA, 3, was placed into a 100 mL flask with a stirbar, 25 mL of ethanol was added and the reaction was heated to 70° C. The hot solution was filtered through a glass wool plug into another 100 mL flask with a stirbar. The solution was kept at 55° C. and a total of 17 mL of water was added dropwise, while the temperature was kept at 55° C. After the water was added, the heat was turned off and the solution cooled slowly to room temperature with stirring. The solid was filtered on a Buchner funnel and washed with 52 mL of 1:1 water:ethanol and then dried overnight under high vacuum to yield 7.5 g of off-white crystals. HPLC analysis showed 99.7% DPA, 3, with 0.3% of the diacid impurity. The solid was dissolved in 25 mL of ethanol at 55° C. and 17 mL of water was added dropwise to maintain the temperature. The heat was turned off and the solution cooled to room temperature slowly. The solid was filtered on a Buchner funnel and washed with 52 mL of 1:1 water:ethanol and then dried overnight under high vacuum to yield 6.8 g of off-white crystals. HPLC analysis showed 100.0% DPA, 3. The overall yield for the two steps in the process was 61% through the first recrystallization and 55.4% after the second recrystallization.

Example 2

Kilo Scale Synthesis

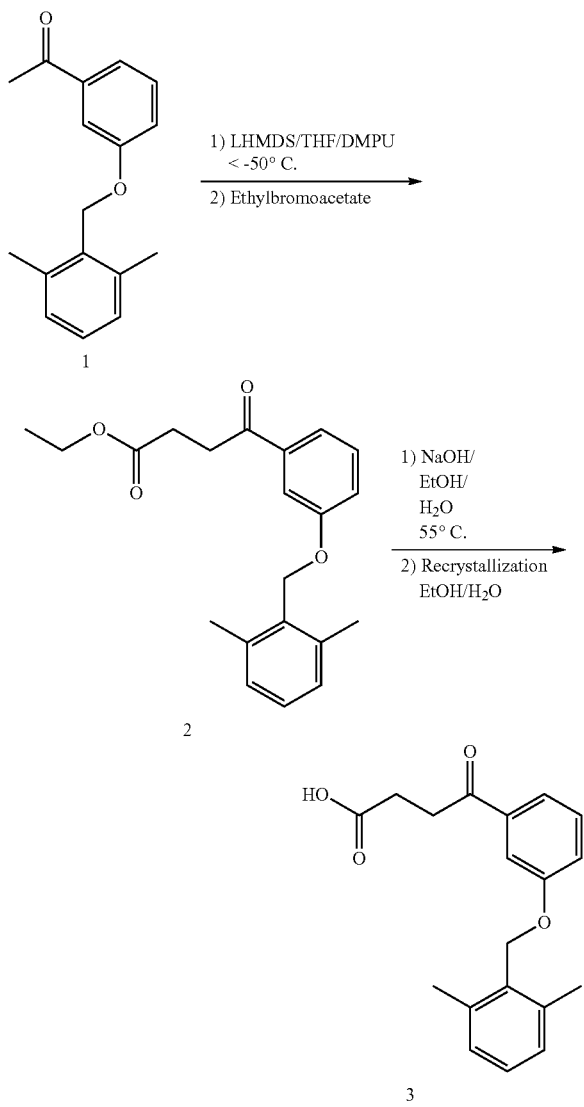

Compound 2:

To a 72 L flask equipped with a reactor head, a stir assembly and a thermocouple, 2.93 kg of 1-[3-(2,6-dimethylbenzyloxy)-phenyl]-ethanone (DPE, 1) (11.52 mol) was added under argon and dissolved into 12.14 L of tetrahydrofuran (THF) and 4.7 L of 1,3-dimethyl-3,4,5,6-tetrahydro-2(1H)-pyrimidinone (DMPU). The total moisture content was brought up to 4.15 mol (0.36 equivalent based on DPE, 1) by adding 54.1 g of water based on the water content of the THF and DMPU. The flask was cooled to below −50° C. in a dry ice/acetone bath and 11.5 L of lithium bis(trimethylsilyl) amide solution (1.19 M in THF, 13.48 mol) was added dropwise over 1 hour keeping the temperature below −50° C. The solution was stirred an additional 30 minutes below −50° C. followed by the dropwise addition of 2.0 L of ethyl bromoacetate (10.04 mol) over 30 minutes to keep the temperature below −50° C. The bath was removed and the solution allowed to warm to −25° C. and was held at this temperature for 10 minutes, allowed to warm to −20° C. and was quenched by the addition of 12 L of 10% ammonium chloride. The aqueous layer was removed, 6 L of ethyl acetate was added, and the organic layer was washed consecutively with 15 L of 4% sodium chloride solution, 15 L of 8% sodium chloride solution, and 15 L of saturated sodium chloride solution. The solution was concentrated to a dark oil. Analysis of the oil showed 78.26 area % of 4-[3-(2,6-dimethylbenzyloxy)-phenyl]-4-oxobutanoic acid ethyl ester (DPAE, 2).

Compound 3:

The dark crude DPAE oil, 2, from three runs (34.56 mol based on starting DPE, 1) was dissolved into a 72 L flask equipped with a reactor head, a stir assembly and a thermocouple using 23.3 L of ethanol. To the solution 2765 g of sodium hydroxide (69.13 mol) dissolved in 10 L of water was added and the reaction was heated with stirring to 55° C. for 30 minutes. The mixture was diluted with 6.0 L of water and concentrated on a rotary evaporator in four portions until ethanol no longer condensed. The aqueous layer was further diluted with 20 L of water and was washed with 4×19 L of methyl t-butyl ether. The solution was acidified stepwise by the addition of 2.0 L of concentrated hydrochloric acid (conc. HCl), addition of 36.7 L of ethyl acetate, and 2.9 L of conc. HCl to lower the pH to approximately pH 1 by test strip analysis. The acidic aqueous layer was removed, and the organic layer was washed with 36.7 L of water and concentrated to 7.58 kg of a beige solid.

Recrystallization: The crude DPA. 3, was placed into a 72 L flask equipped with a reactor head, a stir assembly and a thermocouple and was dissolved into 21.3 L of ethanol and heated to 65° C. The hot solution was filtered directly into a 100 L flask through a medium glass fit. The filtered solution was kept at 55° C. and a total of 15 L of water was added dropwise. After the water was added, the heat was turned off and the solution cooled slowly to room temperature with stirring. The solid was filtered and washed with 10 L of 1:1 water:ethanol on a polyethylene Buchner funnel and then was placed into a 100 L flask. The material was dissolved into 22.3 L of ethanol kept at 55° C. while a total of 15 L of water was added dropwise. After the water was added, the heat was turned off and the solution cooled slowly to room temperature with stirring. The solid was filtered and washed with 10 L of 1:1 water:ethanol on a polyethylene Buchner funnel and then was placed into 6 drying trays in a vacuum oven below 10 torr at 50° C. until a constant weight was achieved. The yield was 6.587 kg of off-white crystals or 61% over the last two steps. HPLC analysis showed 99.92% 4-[3-(2,6-dimethylbenzyloxy)-phenyl]-4-oxobutanoic acid (DPA. 3) with 0.08% DPAE, 2, intermediate. $^1$H NMR (400 MHz, CDCl$_3$); 2.39 (s, 6H); 2.82 (t, 2H); 3.31 (t, 2H); 5.09 (s, 2H); 7.08-7.10 (in, 2H); 7.16-2.25 (m, 2H); 7.40 (t, 1H); 7.59-7.65 (m, 2H).

Example 3

Preparation of 1-[3-(2,6-dimethylbenzyl)-phenyl]-ethanone

To a glass reactor equipped with a reflux condenser, mechanical agitator and nitrogen inlet with bubbler, there was added, under nitrogen, 1.78 kg (11.5 mol) 2,6-dimethylbenzyl chloride, 1.78 kg (12.88 mol) potassium carbonate, 1.57 kg (11.51 mol) 3-hydroxyacetophenone and 9.2 L (8.67 kg) anhydrous N,N-dimethylformamide. The reaction mixture was heated with agitation to 80 to 107 C and held until TLC (Analtech Cat. #02521, silica get GF 250 micron, ⅓ ethyl acetate/hexane) showed the absence of 2,6-dimethylbenzyl chloride. The reaction mixture was cooled over 12 to 18 hr to ambient temperature, 18.4 L of water was added and agitation was continued for 20-30 minutes. Then the reaction mixture was filtered and the precipate was collected. The filter cake was washed with water. The wet filter cake was transferred to a glass reactor equipped with a reflux condenser, mechanical agitator and nitrogen inlet with bubbler. Charged under nitrogen 5.7 L of reagent ethanol and heated at 76-82 C with agitation until all solids were dissolved. Cooled the clear solution to 10 to 15 C with agitation and held for 2-3 hr. Filtered and washed the wet cake 2×2 L, of ½ ethanol/hexanes and 2×1 L hexanes. Dried the wet cake at 45-55C and 25-28 inches of vacuum until a constant weight was achieved. Yield of 1-[3-(2,6-dimethylbenzyl)-phenyl]-ethanone: 86-90% with assay>99%. (For scale-up it could be convenient to replace hexanes with another hydrocarbon solvent to avoid static buildup and flammability issues).

What is claimed is:

1. A method for producing a crude preparation of 4-[3-(2, 6-Dimethylbenzyloxy)phenyl]-4-oxobutanoic acid ethyl ester, comprising:
   (a) to a first solution in a reaction vessel, adding dropwise a second solution while maintaining the solution in the reaction vessel under an inert gas at a temperature below −50° C. under stirring conditions,
      wherein the first solution consists essentially of one equivalent of 1-[3-(2,6-Dimethylbenzyloxy)-phenyl]-ethanone dissolved in tetrahydrofuran and 1,3-Dimethyl-3,4,5,6-tetrahydro-2(1H)-pyrimidinone, the first solution being cooled to a temperature between −35° C. and −75° C. and having a total water content of from 0.1 to 0.6 equivalents; and the second solution consists essentially of from 1.1 to 1.3 equivalents of lithium bis(trimethylsilyl)amide dissolved in tetrahydrofuran;
   (b) stirring the solution resulting from step (a) at a temperature between −35° C. and −75° C. for about 30 minutes;
   (c) to the solution from step (b), adding dropwise from 1 to 2 equivalents of ethyl bromoacetate while maintaining the temperature of the solution in the reaction vessel between −35° C. and −75° C.;
   (d) allowing the temperature of the solution from step (c) to warm to a temperature in a range from −40° C. to 0° C. and maintaining the solution at a temperature in said range for a sufficient time for completion of alkylation;
   (e) adding water or an aqueous salt solution to the solution from step (d) to quench;
   (f) to the organic solution from step (e), adding an organic solvent;
   (g) to the solution from step (f), separating the aqueous layer from the organic layer and discarding the aqueous layer;
   (h) washing the organic layer from the preceding step with a saturated aqueous sodium chloride solution;
   (i) concentrating the organic layer from step (h) to an oil, thereby yielding crude 4-[3-(2,6-Dimethylbenzyloxy)phenyl]-4-oxobutanoic acid ethyl ester.

2. The method of claim 1, wherein the temperature recited in one or more of steps (a), (b) and (c) is below −50° C.

3. The method of claim 1, where in step (a) the first solution has a total water content of 0.36 equivalents.

4. The method of claim 1, where in step (a) the number of equivalents of lithium bis(trimethylsilyl)amide in the second solution is from 1.15 to 1.2.

5. The method of claim 4, wherein the number of equivalents of lithium bis(trimethylsilyl)amide in the second solution is 1.17.

6. The method of claim 1, where in step (c) the number of equivalents of ethyl bromoacetate is from 1.2 to 1.6.

7. The method of claim 6, wherein the number of equivalents of ethyl bromoacetate is from 1.25 to 1.56.

8. The method of claim 1, where in step (d) the solution is maintained at a temperature of −25° C. for about ten minutes.

9. The method of claim 1, where in step (e) the aqueous salt solution is aqueous 10% ammonium chloride.

10. The method of claim 1, where in step (f) the organic solvent is selected from the group consisting of ethyl acetate, ethyl formate, propyl acetate, toluene, and methyl tert-butyl ether.

11. The method of claim 1, further comprising between steps (h) and (i), washing the organic layer from step (h) twice with water or a 4% aqueous solution of either sodium chloride or ammonium chloride.

12. A method for producing a crude preparation of 4-[3-(2, 6-Dimethylbenzyloxy)phenyl]-4-oxobutanoic acid, comprising:
   (a) under stirring conditions in a reaction vessel, dissolving the 4-[3-(2,6-Dimethylbenzyloxy)phenyl]-4-oxobutanoic acid ethyl ester produced by the process of claim 1 in ethanol;
   (b) to the solution from step (a), adding 2 equivalents of sodium hydroxide solution compared to the amount of the ethyl ester and maintaining the solution in the reaction vessel at 55° C. for thirty minutes;
   (c) to the mixture from step (b), adding water and removing the ethanol by evaporation;
   (d) to the solution from step (c), adding water;
   (e) washing the solution from step (d) with methyl t-butyl ether;
   (f) acidifying the solution from step (e) with concentrated hydrochloric acid and ethyl acetate to a pH of between 1 and about 3;
   (g) to the solution from step (f), separating the aqueous layer from the organic layer and discarding the aqueous layer;
   (h) washing the organic layer from step (g) with water;
   (i) concentrating the organic layer from step (h) to a solid, thereby yielding crude 4-[3-(2,6-Dimethylbenzyloxy)phenyl]-4-oxobutanoic acid.

13. The method of claim 12, where in step (f) the pH is between 2 and 3.

14. A method for producing purified 4-[3-(2,6-Dimethylbenzyloxy)phenyl]-4-oxobutanoic acid, comprising:
   (a) in a reaction vessel, dissolving the crude 4-[3-(2,6-Dimethylbenzyloxy)phenyl]-4-oxobutanoic acid produced by the process of claim 12 in ethanol and heating the resulting solution to 65° C.;
   (b) to the solution from the preceding step, adding water dropwise while maintaining the solution at a temperature of from 45° C. to 60° C., wherein the ratio of water added to the amount of ethanol from step (a) is about 4:6;
   (c) allowing the solution from step (b) to cool slowly under stirring conditions to produce a solid; and
   (d) isolating the solid from step (c),
   thereby yielding purified 4-[3-(2,6-Dimethylbenzyloxy) phenyl]-4-oxobutanoic acid.

15. The method of claim 14, further comprising between steps (a) and (b), filtering the solution from step (a) through a medium glass frit.

16. The method of claim 14, where in step (b) the temperature is from 50° C. to 60° C.

17. The method of claim 16, wherein the temperature is from 50° C. to 55° C.

18. The method of claim 17, wherein the temperature is about 55° C.

19. The method of claim 14, where in step (c) the solution is allowed to cool slowly to room temperature.

20. The method of claim 14, further comprising after step (d),
- (e) washing the solid from step (d) with 1:1 water/ethanol;
- (f) dissolving the solid from step (e) in ethanol to produce a solution;
- (g) to the solution from step (f), adding water dropwise while maintaining the solution at 55° C.;
- (h) allowing the solution from step (g) to cool slowly to room temperature under stirring conditions to produce a solid;
- (i) isolating the solid from step (h) and washing the solid with 1:1 water/ethanol;
- (j) drying the solid from step (i),
- thereby yielding further purified 4-[3-(2,6-Dimethylbenzyloxy)phenyl]-4-oxobutanoic acid.

* * * * *

UNITED STATES PATENT AND TRADEMARK OFFICE
CERTIFICATE OF CORRECTION

PATENT NO.       : 8,664,433 B2
APPLICATION NO. : 12/990851
DATED            : March 4, 2014
INVENTOR(S)      : Chinn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 431 days.

Signed and Sealed this

Twenty-ninth Day of September, 2015

Michelle K. Lee
*Director of the United States Patent and Trademark Office*